United States Patent [19]

Welch, Jr.

[11] Patent Number: 4,568,749

[45] Date of Patent: Feb. 4, 1986

[54] CERTAIN 5-ARYL-2-[(4-ARYL)-4-HYDROXYBUTYN-2-YL]-1,2,3,4-γ-CARBOLINES

[75] Inventor: Willard M. Welch, Jr., Mystic, Conn.

[73] Assignee: Pfizer Inc., New York, N.Y.

[21] Appl. No.: 700,795

[22] Filed: Feb. 11, 1985

Related U.S. Application Data

[62] Division of Ser. No. 331,494, Dec. 17, 1981, Pat. No. 4,510,308.

[51] Int. Cl.$^4$ ............................................. C07D 471/04
[52] U.S. Cl. ........................................ 546/85; 546/86
[58] Field of Search ............................. 546/85, 86, 87; 514/292

[56] References Cited

U.S. PATENT DOCUMENTS 4,001,263 1/1977 Plattner et al. ...................... 546/85

OTHER PUBLICATIONS

Midland, J. Org. Chem. 40, pp. 2250–2252 (1975).
Fowler, J. Org. Chem. 42, pp. 2637–2639 (1977).
Komarov et al., Chem. Abs. 79; 4898c (1973).
Zakumbaeva et al., Chem. Abs. 80; 137524v (1974).
Rylander, "Catalytic Hydrogenation over Platinum Metals", Academic Press, New York (1967), pp. 3–5.

Primary Examiner—Alan L. Rotman
Attorney, Agent, or Firm—Charles J. Knuth; Albert E. Frost; Robert K. Blackwood

[57] ABSTRACT

A novel process for preparing various 2-substituted-5-aryl-1,2,3,4-tetrahydro-γ-carboline derivatives is provided, which involves (1) condensing a corresponding 2-unsubstituted compound with formaldehyde and an appropriate acetylenic derivative in the presence of cuprous chloride or cuprous bromide, followed by (2) reduction of the corresponding unsaturated intermediate to yield the desired final product. The latter compounds are known to be useful as tranquilizing agents, with 2-[4-(p-fluorophenyl)-4-hydroxybutyl]-5-(p-fluorophenyl)-8-fluoro-1,2,3,4-tetrahydro-γ-carboline representing a preferred final product. The aforesaid unsaturated intermediates are all novel compounds.

3 Claims, No Drawings

CERTAIN 5-ARYL-2-[(4-ARYL)-4-HYDROXYBUTYN-2-YL]-1,2,3,4-γ-CARBOLINES

This is a division of application Ser. No. 331,494 filed on Dec. 17, 1981 now U.S. Pat. No. 4,510,308 issued Apr. 9, 1985.

BACKGROUND OF THE INVENTION

This invention relates to a new and useful process for preparing various carboline derivatives which are of value in the field of chemotherapy. More particularly, it is concerned with a novel process for preparing certain 2-substituted-5-aryl-1,2,3,4-tetrahydro-γ-carboline derivatives, which are known to be useful as tranquilizing agents. The invention also includes the corresponding 2-unsaturated intermediates, which are novel compounds.

In accordance with the prior art, a number of methods have been presented for preparing compounds of this particular type. For instance, in U.S. Pat. No. 4,001,263 to J. J. Plattner et al., there are described several different synthetic routes leading to the compounds of present interest, of which 2-[4-(p-fluorophenyl)-4-hydroxybutyl]-5-(p-fluorophenyl)-8-fluoro-1,2,3,4-tetrahydro-γ-carboline is an especially preferred embodiment. A typical route disclosed therein for preparing the preferred compounds of this particular class involves (1) treating the corresponding 2-unsubstituted-5-aryl-1,2,3,4-tetrahydro-γ-carboline starting material with an appropriate ω-haloalkyl nitrile in order to effect alkylation at the 2-position of the molecule, followed by (2) reaction of the resulting nitrile compound with an appropriate aromatic Grignard reagent to yield the desired corresponding ketone and then (3) reduction of the ketone with sodium borohydride to yield the desired final product having the requisite secondary alcohol side chain. However, the aforesaid three-step method suffers from a few disadvantages, viz., the use of expensive reagents and the difficulties normally involved upon handling the Grignard reagent and complex metal hydrides, etc., plus the additional time and expense normally caused by the number of steps involved with the overall process.

SUMMARY OF THE INVENTION

In accordance with the present invention, it has now been found possible to prepare various 2-substituted-5-aryl-1,2,3,4-tetrahydro-γ-carbolines by a two-step process which largely circumvents all the aforementioned disadvantages of the prior art. More particularly, the process of this invention involves preparing a compound of the formula:

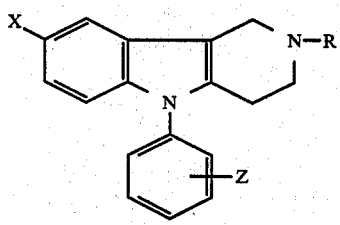

wherein X is hydrogen, fluorine, chlorine or bromine; Z is hydrogen, fluorine, chlorine or methoxy; and R is of the formula

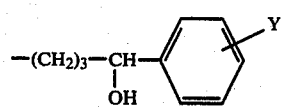

wherein Y is hydrogen, methyl, fluorine or chlorine, which comprises (a) contacting a corresponding 2-unsubstituted-5-aryl-1,2,3,4-tetrahydro-γ-carboline of the formula

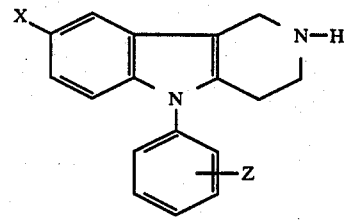

wherein X and Z are each as previously defined, in a reaction-inert polar organic solvent with at least an equimolar amount of an acetylenic compound of the formula

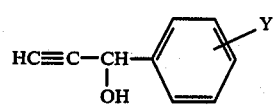

wherein Y is as aforesaid, in the presence of at least an equimolar amount of formaldehyde with respect to said acetylenic compound and in the presence of a catalytically-effective amount of cuprous chloride or cuprous bromide at a temperature that is in the range of from about 20° C. up to about 100° C. until the condensation reaction to form the desired unsaturated intermediate product is substantially complete; and thereafter (b) contacting the acetylenic condensation product formed in step (a) in a reaction-inert organic solvent with hydrogen at a pressure of up to about 75 p.s.i.g. in the presence of a catalytically-effective amount of a noble metal catalyst and at a temperature that is in the range of from about 15° C. up to about 75° C. until the reduction reaction to form the desired final product is substantially complete. In this way, a valuable therapeutic agent, such as 2-[4-(p-fluorophenyl)-4-hydroxybutyl]-5-(p-fluorophenyl)-8-fluoro-1,2,3,4-tetrahydro-γ-carboline (flutroline) is conveniently prepared in a most facile manner.

There is also included within the purview of this invention the novel acetylenic condensation products produced in step (a) as intermediates useful for the production of the final products that have previously been described. The present invention therefore includes novel 2-unsaturated-5-aryl-1,2,3,4-tetrahydro-1,2,3,4-tetrahydro-γ-carboline compounds of the formula:

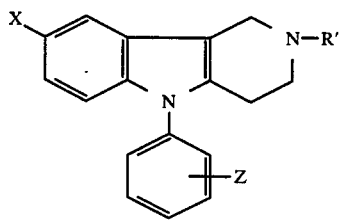

wherein X is hydrogen, fluorine, chlorine or bromine; Z is hydrogen, fluorine, chlorine or methoxy; and R' is of the formula

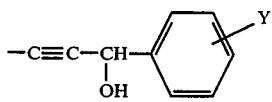

wherein Y is hydrogen, methyl, fluorine or chlorine. Preferred compounds in this category include those of the above formula wherein X, Y and Z are each fluorine and R' is as previously described. A particularly preferred compound for these purposes is 2-[4-(p-fluorophenyl)-4-hydroxybutyn-2-yl]-5-(p-fluorophenyl)-8-fluoro-1,2,3,4-tetrahydro-γ-carboline, as this is the intermediate that specifically leads to flutroline.

DETAILED DESCRIPTION OF THE INVENTION

In accordance with the process of this invention, substantially equimolar amounts of the unsubstituted amine starting material, the acetylenic reagent and formaldehyde are employed in step (a) to effect the condensation reaction, which normally takes place within a period of about one to about 24 hours. The reaction is normally carried out in a reaction-inert polar organic solvent such as a water-miscible lower alkanol like methanol, ethanol or isopropanol, etc., or a cyclic ether of the class including dioxane and tetrahydrofuran, etc. In practice, mixtures of the two type solvents are usually employed. Any convenient source of formaldehyde, such as paraformaldehyde, may be used for the reaction but it is preferable, in practice, to employ the 37% aqueous formaldehyde of commerce, which is commonly known as formalin. However, formaldehyde may also be generated in the reaction mixture in situ by first depolymerizing the readily available paraformaldehyde with concentrated hydrochloric acid. Upon completion of the reaction, the desired 2-unsaturated intermediate is readily recovered from the reaction mixture by first removing the solvents therefrom via evaporation under reduced pressure and then dissolving the resultant residue in a halogenated hydrocarbon solvent such as methylene chloride, followed by washing with dilute acid and base and then subjecting the dried organic extract to evaporation under reduced pressure. In this way, a residual product is obtained that can easily be triturated with a suitable solvent such as acetone and further purified, if necessary, by means of recrystallization in the usual manner from an appropriate solvent system.

The acetylenic condensation product obtained in step (a) is then subjected to catalytic hydrogenation as described in step (b) and this is preferably accomplished by employing a noble metal catalyst such as palladium, usually suspended on a proper catalyst support such as carbon or barium sulfate, etc. The preferred solvent for this reaction is the same as that employed earlier in step (a), viz., a lower alkanol such as methanol or a cyclic ether such as tetrahydrofuran or mixtures thereof. Upon completion of the reduction step, the catalyst is easily separated from the reaction mixture by filtration and the solvent thereafter removed from the resulting filtrate by evaporation under reduced pressure. In this way, a crude residual product is obtained that can then be easily subjected to such standard purification techniques as dissolution in hot ethyl acetate, followed by the addition of n-hexane, etc. so as to afford the desired final product (viz., the 2-substituted-5-aryl-1,2,3,4-tetrahydro-γ-carboline compound) in substantially pure form.

The various 2-unsubstituted-5-aryl-1,2,3,4-tetrahydro-γ-carboline starting materials required for conducting the process of this invention are all known compounds that have previously been prepared and described by J. J. Plattner et al. in U.S. Pat. No. 4,001,263. The required acetylenic reagents are also known compounds which are easily synthesized by treating the appropriate benzaldehyde compound with acetylene in the presence of n-butyl lithium, according to the general procedure described by M. M. Midland in the *Journal of Organic Chemistry*, Vol. 40, No. 15, p. 2250 (1975), to yield the desired 1-hydroxy-1-phenyl-2-propyne.

As previously indicated, the 2-substituted-5-aryl-1,2,3,4-tetrahydro-γ-carboline final products afforded by the process of this invention are all valuable chemotherapeutic agents, useful mainly as tranquilizers, like 2-[4-(p-fluorophenyl)-4-hydroxybutyl]-5-(p-fluorophenyl)-8-fluoro-1,2,3,4-tetrahydro-γ-carboline (flutroline), for example. Hence, they are now provided in pure form and in high yield by the novel process of the present invention, which represents a major contribution to the economy in view of the greatly reduced costs involved.

PREPARATION A

A 200 ml. volume of dry tetrahydrofuran was cooled to −60° C. in a dry ice/acetone bath and then acetylene gas was passed into the solvent until 8.0 g (0.307 mole) had dissolved. The resulting solution was then added to a second 200 ml. portion of dry tetrahydrofuran cooled to −70° C. in a flame-dried 1-liter three-necked, round bottomed reaction flask equipped with magnetic stirrer, addition funnel and nitrogen inlet tube to provide a dry nitrogen atmosphere. To this solution, there was then slowly added 99 ml. of a 2.22 molar solution of n-butyl lithium (0.22 mole) at such a rate that the internal temperature remained below −65° C. After the addition was complete, a solution consisting of 24.82 g (0.20 mole) of p-fluorobenzaldehyde dissolved in 80 ml. of tetrahydrofuran was added at such a rate that the internal temperature again remained below −65° C. The reaction mixture was then stirred at −72° C. for a period of 30 minutes and then allowed to warm up to +5° C. during another 30 minute period. The reaction was then quenched with 80 ml. of water, followed by the addition of anhydrous potassium carbonate to form a pasty mass and an organic supernatant liquid. The organic layer was decanted and combined with two subsequent ether washes of the potassium carbonate mass. The resulting orange solution was then dried over fresh anhydrous potassium carbonate for a period of approximately 16 hours (overnight) and subsequently distilled in vacuo to give 20.5 g (68%) of pure 1-hydroxy-1-(p-fluorophenyl)-2-propyne, b.p. 98°–101° C./8 mm. Hg. A second preparation gave a 92% yield of pure product (b.p. 104° C./9 mm. Hg).

Anal. Calcd. for $C_9H_7FO$: C, 71.98; H, 4.70; F, 12.65. Found: C, 71.71; H, 4.99; F, 12.70.

PREPARATION B

The procedure described in Preparation A is repeated to prepare the following 1-hydroxy-1-phenyl-2-propyne derivatives, starting from the corresponding benzaldehyde compound in each case:
1-hydroxy-1-(o-tolyl)-2-propyne
1-hydroxy-1-(m-tolyl)-2-propyne
1-hydroxy-1-(p-tolyl)-2-propyne
1-hydroxy-1-(o-fluorophenyl)-2-propyne
1-hydroxy-1-(m-fluorophenyl)-2-propyne
1-hydroxy-1-(o-chlorophenyl)-2-propyne
1-hydroxy-1-(m-chlorophenyl)-2-propyne
1-hydroxy-1-(p-chlorophenyl)-2-propyne

EXAMPLE 1

A solution consisting of 9.47 g. (0.033 mole) of 5-(p-fluorophenyl)-8-fluoro-1,2,3,4-tetrahydro-γ-carboline (prepared according to the procedure described by J. J. Plattner et al. in U.S. Pat. No. 4,001,263) dissolved in 150 ml. of absolute ethanol was placed in a 500 ml. reaction flask under a dry nitrogen atmosphere and warmed to ~35° C., and then treated with 2.78 ml. of a 37% aqueous formaldehyde solution (0.033 mole) and 1.64 g. of cuprous chloride. As soon as the reaction mixture became homogeneous (a period of 1–2 minutes), a solution consisting of 5.0 g. (0.033 mole) of 1-hydroxy-1-(p-fluorophenyl)-2-propyne (prepared as described in Preparation A) dissolved in 80 ml of dioxane was added. The resulting mixture was then stirred overnight at ambient temperature for a period of approximately 16 hours. At the end of this time, the solvents were removed in vacuo and the residues subsequently dissolved in 300 ml. of methylene chloride. After washing with dilute hydrochloric acid and dilute ammonium hydroxide, the organic phase was dried over anhydrous magnesium sulfate and filtered. The resulting filtrate was then evaporated to near dryness while under reduced pressure and the residue thus obtained was subsequently treated with 100 ml. of acetone to form a slurry. The pale yellow solid which resulted was thereafter recovered by means of suction filtration and subsequently recrystallized from 400 ml. of acetone and 100 ml. of methanol to give 5.8 g. (39%) of pure 2-[4-(p-fluorophenyl)-4-hydroxybutyn-2-yl]-5-(p-fluorophenyl)-8-fluoro-1,2,3,4-tetrahydro-γ-carboline, m.p. 194°–196° C.

Anal. Calcd. for $C_{27}H_{21}F_3N_2O$: C, 72.63; H, 4.72; N, 6.27. Found: C, 72.33; H, 4.94; N, 6.39.

EXAMPLE 2

The procedure described in Example 1 is repeated to prepare the following 2-(4-phenyl-4-hydroxybutyn-2-yl)-5-phenyl-1,2,3,4-tetrahydro-γ-carboline derivatives, starting from the corresponding 2-unsubstituted-5-phenyl-1,2,3,4-tetrahydro-γ-carboline base and the appropriate 1-hydroxy-1-phenyl-2-propyne derivative in each instance:
2-[4-(p-tolyl)-4-hydroxybutyn-2-yl]-5-(p-fluorophenyl)-8-fluoro-1,2,3,4-tetrahydro-γ-carboline
2-[4-(m-fluorophenyl)-4-hydroxybutyn-2-yl]-5-(p-fluorophenyl)-8-fluoro-1,2,3,4-tetrahydro-γ-carboline
2-[4-(p-fluorophenyl)-4-hydroxybutyn-2-yl]-5-(o-fluorophenyl)-8-fluoro-1,2,3,4-tetrahydro-γ-carboline
2-[4-(p-fluorophenyl)-4-hydroxybutyn-2-yl]-5-(m-fluorophenyl)-8-fluoro-1,2,3,4-tetrahydro-γ-carboline
2-[4-(p-chlorophenyl)-4-hydroxybutyn-2-yl]-5-(p-fluorophenyl)-8-fluoro-1,2,3,4-tetrahydro-γ-carboline
2-[4-(p-tolyl)-4-hydroxybutyn-2-yl]-5-(p-fluorophenyl)-8-chloro-1,2,3,4-tetrahydro-γ-carboline
2-[4-(p-fluorophenyl)-4-hydroxybutyn-2-yl]-5-phenyl-8-chloro-1,2,3,4-tetrahydro-γ-carboline
2-[4-(p-fluorophenyl)-4-hydroxybutyn-2-yl]-5-(p-fluorophenyl)-8-chloro-1,2,3,4-tetrahydro-γ-carboline
2-[4-(p-fluorophenyl)-4-hydroxybutyn-2-yl]-5-(p-anisyl)-8-fluoro-1,2,3,4-tetrahydro-γ-carboline.

EXAMPLE 3

A solution consisting of 100 mg. (0.000245 mole) of 2-[4-(p-fluorophenyl)-4-hydroxybutyn-2-yl]-5-(p-fluorophenyl)-8-fluoro-1,2,3,4-tetrahydro-γ-carboline dissolved in 10 ml. of dry tetrahydrofuran was treated with 100 mg. of 5% palladium on barium sulfate catalyst and stirred in a hydrogen atmosphere for a period of 90 minutes. At the end of this time, the catalyst was separated from the reaction mixture by means of filtration and the solvent thereafter removed by means of evaporation under reduced pressure to afford a crude residual product. The latter material was then dissolved in 1.0 ml. of hot ethyl acetate and the resulting solution subsequently diluted with 15 ml. of n-hexane to give, upon cooling, 65 mg. (65%) of pure 2-[4-(p-fluorophenyl)-4-hydroxybutyl]-5-(p-fluorophenyl)-8-fluoro-1,2,3,4-tetrahydro-γ-carboline in the form of a crystalline deposit. The pure product melted at 143°–144° C. and was identical in every respect with an authentic sample prepared according to the procedure described in U.S. Pat. No. 4,001,263, as shown by thin layer chromatography.

EXAMPLE 4

The procedure described in Example 3 is repeated to prepare the following 2-(4-phenyl-4-hydroxybutyl)-5-phenyl-1,2,3,4-tetrahydro-γ-carboline derivatives, starting from the corresponding 2-(4-phenyl-4-hydroxybutyn-2-yl)-5-phenyl-1,2,3,4-tetrahydro-γ-carboline compound in each case:
2-[4-(p-tolyl)-4-hydroxybutyl]-5-(p-fluorophenyl)-8-fluoro-1,2,3,4-tetrahydro-γ-carboline
2-[4-(m-fluorophenyl)-4-hydroxybutyl]-5-(p-fluorophenyl)-8-fluoro-1,2,3,4-tetrahydro-γ-carboline
2-[4-(p-fluorophenyl)-4-hydroxybutyl]-5-(o-fluorophenyl)-8-fluoro-1,2,3,4-tetrahydro-γ-carboline
2-[4-(p-fluorophenyl)-4-hydroxybutyl]-5-(m-fluorophenyl)-8-fluoro-1,2,3,4-tetrahydro-γ-carboline
2-[4-(p-chlorophenyl)-4-hydroxybutyl]-5-(p-fluorophenyl)-8-fluoro-1,2,3,4-tetrahydro-γ-carboline
2-[4-(p-tolyl)-4-hydroxybutyl]-5-(p-fluorophenyl)-8-chloro-1,2,3,4-tetrahydro-γ-carboline
2-[4-(p-fluorophenyl)-4-hydroxybutyl]-5-phenyl-8-chloro-1,2,3,4-tetrahydro-γ-carboline
2-[4-(p-fluorophenyl)-4-hydroxybutyl]-5-(p-fluorophenyl)-8-chloro-1,2,3,4-tetrahydro-γ-carboline 2-[4-(p-fluorophenyl)-4-hydroxybutyl]-5-(p-anisyl)-8-fluoro-1,2,3,4-tetrahydro-γ-carboline.

I claim:

1. A 2-unsaturated-5-aryl-1,2,3,4-tetrahydro-γ-carboline compound of the formula:

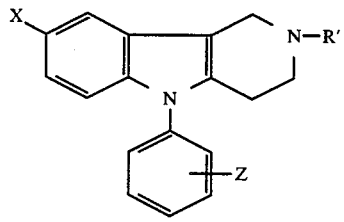

wherein
X is hydrogen, fluorine, chlorine or bromine;
Z is hydrogen, fluorine, chlorine or methoxy; and
R' is of the formula:

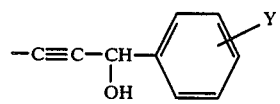

wherein
Y is hydrogen, methyl, fluorine or chlorine.

2. A compound as claimed in claim 1 wherein X, Y and Z are each fluorine.

3. 2-[4-p-Fluorophenyl)-4-hydroxybutyn-2-yl]-5-(p-fluorophenyl)-8-fluoro-1,2,3,4-tetrahydro-γ-carboline.

* * * * *